(12) United States Patent  (10) Patent No.: US 9,956,160 B2
Luu  (45) Date of Patent: May 1, 2018

(54) GEL POLISH THINNER

(71) Applicant: Le Chat, Hercules, CA (US)

(72) Inventor: Newton Luu, Hercules, CA (US)

(73) Assignee: LeChat, Hercules, CA (US)

( * ) Notice: Subject to any disclaimer, the term of this patent is extended or adjusted under 35 U.S.C. 154(b) by 0 days. days.

(21) Appl. No.: 13/839,333

(22) Filed: Mar. 15, 2013

(65) Prior Publication Data

US 2014/0261508 A1 Sep. 18, 2014

(51) Int. Cl.
*A61K 8/81* (2006.01)
*A45D 29/20* (2006.01)
*A61K 8/55* (2006.01)
*A61Q 3/02* (2006.01)
*A61K 8/35* (2006.01)
*A61K 8/86* (2006.01)

(52) U.S. Cl.
CPC .............. *A61K 8/8152* (2013.01); *A61K 8/35* (2013.01); *A61K 8/55* (2013.01); *A61K 8/86* (2013.01); *A61Q 3/02* (2013.01)

(58) Field of Classification Search
None
See application file for complete search history.

(56) References Cited

U.S. PATENT DOCUMENTS

| | | | |
|---|---|---|---|
| 5,637,292 A * | 6/1997 | Thomas | 424/61 |
| 5,639,447 A | 6/1997 | Patel | |
| 5,700,576 A * | 12/1997 | Brehm | C09D 4/06 428/412 |
| 5,716,603 A | 2/1998 | Chen et al. | |
| 6,051,242 A | 4/2000 | Patel | |
| 6,455,033 B1 | 9/2002 | Steffier | |
| 2002/0197218 A1 | 12/2002 | Bernard et al. | |
| 2003/0091519 A1 | 5/2003 | Zatz et al. | |
| 2010/0028701 A1* | 2/2010 | De Cooman et al. | 428/480 |
| 2011/0182837 A1 | 7/2011 | Steffier | |
| 2011/0226271 A1 | 9/2011 | Raney | |
| 2011/0256079 A1 | 10/2011 | Kozachek | |
| 2011/0256080 A1 | 10/2011 | Kozachek et al. | |
| 2011/0277338 A1 | 11/2011 | Li et al. | |
| 2012/0004340 A1 | 1/2012 | Raney | |
| 2012/0197172 A1 | 8/2012 | Ogawa | |
| 2012/0252710 A1 | 10/2012 | Steffier et al. | |
| 2013/0025617 A1 | 1/2013 | Raney | |
| 2013/0034512 A1 | 2/2013 | Kozachek | |
| 2013/0059411 A1* | 3/2013 | Gerard | C08F 287/00 438/66 |

FOREIGN PATENT DOCUMENTS

| KR | 10-2012-0090055 A1 | 8/2012 |
|---|---|---|
| WO | 2011-115795 A2 | 9/2011 |
| WO | 2012-163851 A2 | 12/2012 |

OTHER PUBLICATIONS

Seche Restore <http://www.salonsupplystore.com/seche-restore-coat-nail-restoration-p-669783.html?osCsid=8a3334cc95136516a44132e5ca9a4a0c>, Accessed Apr. 15, 2014, Available online Oct. 25, 2012.*
Sigma Aldrich. Applications: Free Radical Initiators, <https://www.sigmaaldrich.com/content/dam/sigma-aldrich/docs/Aldrich/General_Information/photoinitiators.pdf> available Feb. 1, 2001; accessed Jul. 29, 2016.*
International Search Report, PCT Application PCT/US2014/030735, dated Aug. 7, 2014, 3 pages.
Written Opinion, PCT Application PCT/US2014/030735, dated Aug. 7, 2014, 4 pages.

* cited by examiner

*Primary Examiner* — Nicole P Babson
(74) *Attorney, Agent, or Firm* — Aka Chan LLP

(57) ABSTRACT

A composition for a thinning agent to reduce the viscosity of a traditional gel or gel polish includes at least one monomer and a photoinitiator. The thinner can reduce the viscosity of a gel polish that has thickened, and allow for easy application of the gel to the nails. Aspects of the thinner can cause a ultra-violet curable gel or gel polish, using a ultra-violet light, to cure using a ultra-violet light emitting diode light source, when the thinner is added to the gel. The thinner is versatile and can be added to any gel polish or traditional gel to extend the life of the gel.

21 Claims, No Drawings

GEL POLISH THINNER

BACKGROUND OF THE INVENTION

The invention relates to the field of radiation-curable gel polish and gel products, and in particular, to a composition for a gel polish thinner.

Radiation-curable gel systems for manicures and pedicures have increased in availability and popularity in recent years. There are advantages to traditional gels and gel polishes that are not available to conventional nail polish. Under a ultra-violet radiation (UV) or light emitting diode (LED) light, gel polishes can cure in minutes while regular nail polish takes longer cure. Gel polishes can last for up to two to three weeks without fading or chipping. In contrast, ordinary nail polish can chip, peel, crack, and begin to fade within one to days. Gel polishes can produce a finish that is not only resilient to wear, but can also have a high gloss look, which creates a shiny and smooth looking appearance on the nails.

The physical and chemical properties of gels change over time. Gel polishes contained in bottles or other containers can age and become more viscous (i.e., thicken) with time (such as due to evaporation). A more viscous gel is difficult to apply to the nail, and cause defects in the finish. For example, streaking, poor color dispersion, and leveling of the surface are common problems.

Gels are cured (i.e., dry) using radiation. UV radiation is the most conventional form of radiation used to cure gels. Professional nail technicians typically apply UV curable gels that require curing under a UV lamp (e.g., compact fluorescent lamp (CFL)). LED lamps can also be used to cure UV/LED curable gels that specifically require an LED light. UV LED curable gels cure significantly faster in LED light than in UV/CFL light. Thus, UV LED curable gels are preferred by many customers and nail technicians.

Therefore, there is a need for a thinning agent that reduces the viscosity of gel polishes as well as allowing UV curable gels, typically used with a UV CFL lamp, to be used with a UV LED lamp for a faster curing time. The thinner will not reduce the potency of the gel, and will allow for easy application of the gel to the nails.

BRIEF SUMMARY OF THE INVENTION

A composition for a thinning agent to reduce the viscosity of a traditional gel or gel polish includes at least one monomer and a photoinitiator. The thinner can reduce the viscosity of a gel polish that has thickened, and allow for easy application of the gel to the nails. The thinner is versatile and can be added to any gel polish or traditional gel to extend the life of the gel.

A composition for a gel thinner can have a viscosity of about 1.002 centipoise (i.e., 0.01002 poise) to about 100 centipoise at 20 degrees Celsius. The relatively lower viscosity of the thinner can help reduce a greater viscosity of the gel polish.

In a specific implementation, a composition for a gel polish thinner includes hydroxyethyl methacrylate, isobornyl methacrylate, hydroxycyclohexyl phenyl ketone, 2,4,6-trimethylbenzoyldiphenylphosphine oxide, ethoxylated trimethylolpropane triacrylate esters (ETPTA), and alkoxylated diacrylate. In other implementations, the composition can include any one or more of the ingredients, in any combination.

In a specific implementation, the composition for the thinner can include a photoinitiator. When added to the polish, the thinner does not dilute the effects of a photoinitiator of the gel polish. This allows for the gel polish to maintain its original curing time.

Aspects of the thinner can cause a UV-curable gel or gel polish, using UV CFL light, to cure using a UV LED light. This can reduce the cure time from about an average of three minutes to about 30 seconds for a layer of gel. Aspects of the invention are also applicable to other gel products for manicures and pedicures including traditional gels, sculpting gels, and other.

In a kit comprising a gel nail polish thinner, the kit includes the thinner solution as described in this application contained within a bottle (e.g., which can be made of glass, polycarbonate, plastic, or other material that does not chemically react with the thinner). The bottle can be opaque, which prevents the transmission of light through to the thinner that might activate the photoinitiator compounds in the thinner. In other implementations, the bottle can be colored, such as in a brown (e.g., translucent brown), amber, blue, or other color, to prevent transmission of light wavelengths through to the thinner that would activate the photoinitiator. The bottle can include a cap with eyedropper (e.g., clear glass), which will help more accurately measure a number of drops being added to thin a gel nail polish. The bottle can hold 1 ounce (30 milliliters) of thinner. Other sizes more or less than 1 ounce are available, such as 1.5, 2, 3, 3.5, 4, and 8 ounces and others. The bottle can be contained within a box, which is used to ship the thinner. The box can include a cutout (e.g., rounded rectangle) which allows a customer to view the label of the bottom without needing to remove the bottle from the box.

The box and bottle can include labeling with directions on how to use the product. The product packaging may be marked with a flammable symbol (to indicate its flammability) and a period after opening (PaO) symbol (e.g., indicating that the product remains usable for, e.g., 12 months after opening). The cap provides an airtight seal and is delivered in vacuum sealed. After opening, the cap prevents the volatile components of the thinner from evaporating.

A specific implementation of a gel nail polish thinner of the invention is a product by LeChat Nail Care Products known as Gelos™ (item number GLST01). Gelos is non-solvent gel thinner. Gelos restores gel that has thickened while maintaining its original curing time. Gelos can be used with any gel polish or traditional gel to extend the life of the product. Directions for use: Add 3-4 drops of thinner into the gel bottle to be thinned. Mix well. Repeat as necessary for desired consistency. A warning is to keep the thinner away from direct sunlight and UV light. More information on Gelos and other products can be found on the LeChat Web site, www.lechatnails.com, which is incorporated by reference, along with product briefs and white papers on Gelos.

Other objects, features, and advantages of the present invention will become apparent upon consideration of the following detailed description and the accompanying drawings, in which like reference designations represent like features throughout the figures.

DETAILED DESCRIPTION OF THE INVENTION

A gel nail polish thinner is added to a gel nail polish to reduce its viscosity (e.g., shear viscosity). For example, a nail polish from a given manufacturer may be too viscous or thick for a particular application. A gel nail polish thinner is used to thin this polish before application. In another example, a nail polish thinner is a chemical composition that restores thickened nail polish to its original consistency and can help to prolong the life of the polish.

Gel polish that is too thick may result in a polish that is difficult to apply and does not last as long on the nail as a polish that is the correct consistency. Sculpting or builder gels are typically very difficult to apply due to their high viscosity and they often need to be filed down and reapplied multiple times to build up a nail. In contrast, lower viscosity UV curable gels can be applied as a thin coat and are typically applied as a single coating. A second coating is optional.

But even bottles of lower viscosity UV curable gel can become thicker over time due to evaporation or extended exposure to light (e.g., due to repeated bottle openings). Then, even the lower viscosity curable gels becomes too thick, and suffer the same difficulty in applying as sculpting or builder gels. A gel nail polish thinner can be used to thin this thickened gel polish. The gel polish can be thinned to a viscosity as desired. For example, by adding 1, 2, 3, 4, or other number of drops of thinner to the gel polish as desired, the viscosity of the gel polish will be reduced. The greater number of drops of thinner added, the less viscous the gel polish will become.

The gel nail polish thinner has a typical viscosity of about 1.002 centipoise (i.e., 0.01002 poise), at 20 degrees Celsius. This is approximately the same viscosity of water. If applied to a nail directly, this gel nail polish thinner will run off the nail because it is not sufficiently viscous, unlike a gel polish. In comparison, a lower viscosity gel polish can have a viscosity from about 20 to about 70 poise, which is at least an order of magnitude greater than the thinner. The thinner can be added to the polish to lower the viscosity to a level as desired by the user.

Although lower viscosity gels (e.g., 20-70 poise) are desirable, the use of lower viscosity gels can lead to colored gel formulations having a limited shelf life due to pigment settling and the formation of hard packs. Gel nail polish thinners were previously unavailable. So, once the hard pack is formed, it is difficult or nearly impossible to resuspend the pigment into the gel as a homogeneous composition. The availability of a gel nail polish thinner avoids this previous problem.

A composition for a thinning agent to reduce the viscosity of a gel polish includes at least one monomer. In other implementations, the composition can also include an oligomer, and a photoinitiator. The thinner can reduce the viscosity of a gel polish that is thicker than desired or has thickened, while maintaining the gel polish's original curing time or improving the curing time (e.g., speeding up curing). The thinner is versatile and can be added to any gel polish or traditional gel to extend the life of the gel.

Traditional gels and gel polishes can be applied to natural nails (e.g., fingernails and toenails), artificial fingernails, toenails, and artificial nail extensions to build up the thickness of the nail. Gels can be more viscous than traditional nail polish. For example, the viscosity of a regular gel resin used in UV-cured nail products can range from about 25,000 centipoise (cP) to about 100,000 centipoise. A nail builder gel can have a higher viscosity than regular gel that is about 350,000 centipoise. Some builder gels can have a viscosity as high as 1,000,000 cP.

The composition for the gel polish thinner can have a viscosity of about 1.002 centipoise to about 10 centipoise at 20 degrees Celsius (i.e., about room temperature). At 25 degrees Celsius, the thinner can have a lower viscosity of about 0.89 centipoise. In addition to the chemical properties of the compounds in the composition, the relatively lower viscosity of the thinner can reduce the greater viscosity of the gel polish.

In other implementations, the viscosity of the thinner can range from about 1 centipoise to about 100 centipoise. The viscosity for example, can be from about 10 to about 100 centipoise, from about 50 to about 200 centipoise, from about 200 to about 500 centipoise, about 300 to about 700 centipoise, about 700 to about 1000 centipoise, or other ranges. As the viscosity of the thinner increases, the amount necessary to reduce the thickness of a nail polish will increase. While a single drop, a thinner with a viscosity of 1 centipoise can reduce the viscosity of a gel polish significantly, while a single drop of a 700 centipoise thinner will reduce viscosity less so. The thinner can be provided in a variety of viscosities to provide greater control in the resulting viscosity of the thinned gel.

While thinning a gel, a gel thinner can also affect the curing properties of the gel polish. This is because the thinner reduces the concentration of the photoinitiator in the thinned gel. Then, longer curing times will be needed. In a specific implementation, the gel nail polish thinner includes photoinitiator. With the photoinitiator in the thinner, the thinned gel polish will have improved curing times over a gel thinned without the photoinitiator.

Traditional gels and gel polish contain a photoinitiator ingredient that absorbs light and converts the light into the energy needed to cure the gel, through the polymerization of other chemical components of the gel. Different photoinitiators are activated at different wavelengths of light, and can affect the curing process. For example, a photoinitiator that is activated by a longer wavelength of UV light can allow the light to penetrate deep into the lower layers of the gel on the nail. Certain photoinitiators can be used for UV LED-curable gels, while different photoinitiators can be used for traditional UV-curable gels.

In an implementation, the thinner includes photoinitiator, which is added to the gel polish when thinning. Then the gel will have improved curing time compared to using a thinner without photoinitiator. In an implementation, the photoinitiator in the thinner is sufficient in concentration so the thinned gel will maintain its original curing time after the thinner is added. Alternatively, the concentration of photoinitiator is sufficient to improve upon the original curing time of the gel. A typical cure time for a layer of UV-cured gel polish is about three or more minutes.

The type of photoinitiator in the thinner can vary. There are photoinitiators which are curable in a light wavelength of about 350 nanometers. There are photoinitiators which are curable in a light wavelength of about 375 nanometers. One or both photoinitiators types, or other photoinitiator types reactive at different wavelengths, can be added to the thinner.

In a specific implementation, a thinner includes a photoinitiator reactive at the light wavelength of about 375 nanometers (as an example). This can be added to a gel polish that has photoinitiator at a different wavelength, other than 375 nanometers. Then, the thinned gel polish will cure using a lamp emitting 375 nanometers, when it previously was not reactive to light at this wavelength.

In this way, the thinner can make a UV-curable gel or gel polish (using UV CFL light) cure using a UV LED light. Typically, such UV-curable gels cannot also be cured using a UV LED light since a photoinitiator in the UV-curable may not be activated by LED light, which tends to be emitted at a narrow range than UV CFL light.

On the electromagnetic spectrum, UV light is between about 100 nanometers to about 400 nanometers. UV lamps use bulbs that are compact fluorescents lamps. The wavelength on LED lights is much narrower than that of the UV CFL. This narrow wavelength emits the right amount of the specific UV-A wavelength that is needed to cure UV LED-curable gels. So, LED-curable gels typically cure faster in LED lights than in UV CFL lights.

For example, typically, UV-curable gels require light of a wavelength of about 350 nanometers to cure. UV lamps can emit light in a wavelength of about 320 to about 400 nanometers. However, an LED-curable gel that requires light of 375 nanometers to cure will use a lamp that emits from only 370 to 380 nanometers.

The LED lamp that emits at 370 to 380 nanometers will not cure the gel with a 350 nanometer reactive photoinitiator, but will cure the thinned gel with both photoinitiators at 350 and 375 nanometers. The UV lamp that emits light at 320 to 400 nanometers will also cure the thinned gel with both photoinitiators at 350 and 375 nanometers. Therefore, in effect, by use of the thinner, the gel polish has become "converted" into a LED lamp curable gel when it previously was not.

The cure time for gels using a UV LED light can be significantly faster since LED bulbs emit a narrower wavelength range of light. The light is more targeted to the photoinitiator in the gel. An average cure time for a layer of UV LED-curable gel polish is about 30 seconds to about 1 minute, while the average cure time for a UV CFL-curable gel is about three minutes or more.

In a specific implementation where a photoinitiator is included in the thinner, special containers can be used to contain the thinner in order to minimize exposure to light. After repeated exposure over time, the photoinitiator can make the thinner become more viscous. In specific implementations, the container includes a bottle that is a dark color (e.g., black, brown, dark blue, dark purple, dark grey, dark green, dark red, and many others) to prevent light from transmitting through, or otherwise coming into the bottle. The bottle can be made of an unreactive material such as glass. In other implementations, the container is opaque and does not transmit light through the walls of the container.

The thinner container can include a mechanism to allow a user to add the thinner to the gel polish container in a controlled way. In a specific implementation, the container includes a dropper. This allows the user to add a desired number of drops to the gel container. In other implementations, various other types of mechanisms can be used including for example, a built-in dropper (e.g., dropper is incorporated into the container), a removable dropper (e.g., dropper is in a cap of the container), an eye dropper, a pipette, a spout, and others.

The composition does not depend on solvents to dilute the gel polish. Conventional nail polish thinners rely on one or more solvents as the primary active ingredients. For example, typical solvents include acetone, butyl acetate, toluene, methyl ethyl ketone, hexane, isopropyl alcohol, heptane, or any combination of these. These ingredients can be added to the original nail polish to reduce thickness. However, disadvantages associated with these commonly used solvents can cause undesirable effects such as evaporation. These solvent-based thinners can evaporate over time, both before and after being added to the polish. In contrast, the composition for the gel polish thinner does not use solvents as the primary active ingredients. Hence, the thinner does not evaporate when it is contained by itself prior to addition to a gel. And it does not evaporate from the gel polish after it has been added into the gel.

In a specific implementation, a composition for a gel polish thinner includes hydroxyethyl methacrylate, isobornyl methacrylate, hydroxycyclohexyl phenyl ketone, 2,4,6-trimethylbenzoyldiphenylphosphine oxide, ethoxylated trimethylolpropane triacrylate esters (ETPTA), and alkoxylated diacrylate. In other implementations, the composition can include any one or more of the ingredients, in any combination. Other ingredients (and their equivalents) can be substituted for or replace any of the one or more of the listed ingredients.

The composition in these implementations is not limited to the specific ingredients presented. A composition of the invention may have additional compounds (not necessarily described in this application), different compounds which replace some of the compounds presented, fewer of the compounds presented, or any combination of these. For example, hydroxyethyl methacrylate and hydroxycyclohexyl phenyl ketone can be combined with other ingredients (not presented above) such as other reactive monomers (e.g., esters and amides of acrylic and methacrylic acid, including hydroxypropyl methacrylate, trimethylolpropane trimethacrylate, and many others), and photoinitiators (e.g., benzyl ketones, monomeric hydroxyl ketones, polymeric hydroxyl ketones, alpha-amino ketones, acyl phosphine oxides, metallocenes, benzophenone, benzophenone derivatives, and many others). In these implementations, various ingredients other than those presented above can be used in combination with hydroxyethyl methacrylate and hydroxycyclohexyl phenyl ketone.

Table A below provides the range of amount (percentage by weight) of each ingredient that can be used, while still maintaining its efficacy as a thinning agent. It should be understood that the invention is not limited to the specific percentages presented. A formulation of the invention may have additional compounds (not necessarily described in this application), different compounds which replace some of the compounds presented, fewer of the compounds presented, or any combination of these. Further, the compounds in other implementations of the invention may not be exactly the same as the compounds presented and may be modified or altered as appropriate for a particular application or based on the data or situation. For example, the percentages can also be specified by volume.

TABLE A

| Ingredient | Range (Percentage by Weight (% WT/WT)) |
|---|---|
| Hydroxyethyl methacrylate (HEMA) | 25-35 |
| Isobornyl methacrylate | 20-30 |
| Hydroxycyclohexyl phenyl ketone | 20-30 |
| 2,4,6-trimethylbenzoyldiphenylphosphine oxide | 10-15 |
| Ethoxylated trimethylolpropane triacrylate esters (ETPTA) | 1-5 |
| Alkoxylated diacrylate | 1-5 |

In a specific implementation, the thinner composition includes no pigment or mixture of pigments, reactive monomers selected from one or more ethylenically unsaturated monomers, and one or more ethylenically unsaturated oligomers, or mixtures of these, and a photoinitiator. A final viscosity of the thinner is in a range from about 0.01 poise to about 2 poise. No thixotropic additives are needed.

The composition for the gel thinner can include various compounds containing one or more polymerizable unsaturated double bonds. Typical examples include esters and amides of acrylic and methacrylic acid. In a specific implementation, hydroxyethyl methacrylate (HEMA) monomer can be included in the composition. When polymerized, HEMA includes properties such as adhesion to substrates and crosslinking sites.

In another specific implementation, isobornyl methacrylate monomer can be included in the composition. It can be used as a diluent monomer in radiation curable formulations to increase abrasion resistance, gloss, and hardness.

In yet another specific implementation, ethoxylated trimethylolpropane triacrylate esters (ETPTA) can be included in the composition.

In another specific implementation, alkoxylated diacrylate is included in the composition. It is a monomer that can be used to reduce viscosity, improve pigment dispersion stability, enhances flow, and allows easy pigment redispersion and fast cure response.

The composition for the gel thinner can include one or more photoinitiators. In a specific implementation, the composition includes hydroxycyclohexyl phenyl ketone and 2,4,6-trimethylbenzoyldiphenylphosphine oxide, individually or in combination. Other photoinitiators (and their equivalents) can be substituted for or replace any of the one or more of the photoinitiators presented. Examples of photoinitiators include: benzyl ketones, monomeric hydroxyl ketones, polymeric hydroxyl ketones, alpha-amino ketones, acyl phosphine oxides, metallocenes, benzophenone, benzophenone derivatives, and the like. Specific examples include: 1-hydroxy-cyclohexylphenylketone, benzophenone, 2-benzyl-2-(dimethylamino)-1-(4-(4-morpholinyl) phenyl)-1-butanone, 2-methyl-1-(4-methylthio)phenyl-2-(4-morpholinyl)-1-propanone, diphenyl-(2,4,6-phosphine oxide, phenyl bis(2,4,6-trimethylbenzoyl) phosphine oxide, benzyl-dimethylketal, isopropylthioxanthone, and any combination of these.

This description of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications. This description will enable others skilled in the art to best utilize and practice the invention in various embodiments and with various modifications as are suited to a particular use. The scope of the invention is defined by the following claims.

The invention claimed is:

1. A gel nail polish thinner comprising reactive monomers comprising
a first monomer comprising hydroxyethyl methacrylate,
a second monomer comprising isobornyl methacrylate,
a third monomer comprising ethoxylated trimethylolpropane triacrylate esters,
a fourth monomer comprising alkoxylated diacrylate,
a first photoinitiator, wherein the first photoinitiator comprises hydroxycyclohexyl phenyl ketone that is responsive to a light of a first ultraviolet wavelength, and
a second photoinitiator, wherein the second photoinitiator comprises 2, 4, 6-trimethylbenzoyldiphenylphosphine oxide that is responsive to a light of a second ultraviolet wavelength, which is different from the first ultraviolet wavelength,
wherein the thinner comprises no pigment, no solvent, and no oligomers, and the viscosity of the thinner is in the range of 0.01 poise to 2 poise, and
when the thinner is subjected to ultraviolet light of at least one of the first or second ultraviolet wavelength, a polymerization reaction will occur,
wherein before the polymerization reaction occurs, the fourth monomer acts as a pigment redispersant for a pigment in a gel nail polish to which the thinner is added, and
during the polymerization reaction, the first and second monomers react to form long, straight polymer chains, and the third and fourth monomers react to crosslink the long, straight polymer chains into a net-like polymeric structure.

2. The gel nail polish thinner of claim 1 wherein the weight percentage of the first monomer is in the range of 25 to 35 weight percent, the weight percentage of the second monomer is in the range of 20 to 30 weight percent, the weight percentage of the third monomer is in the range of 1 to 5 weight percent, and the weight percentage of the fourth monomer is in the range of 1 to 5 weight percent.

3. The gel nail polish thinner of claim 2 wherein the weight percentage of the first photoinitiator is in the range of 20-30 weight percent, and the weight percentage of the second photoinitiator is in the range of 10-15 weight percent.

4. A thinner for a gel nail polish comprising:
only nonmetallic monomers comprising at least a first monomer and a second monomer, different from the first monomer; and
at least a first photoinitiator and a second photoinitiator, which is different from the first photoinitiator;
wherein the viscosity of the thinner is about 1 centipoise to about 10 centipoise, the composition does not comprise a solvent and does not comprise oligomers, wherein the thinner is added to the gel nail polish to reduce the viscosity of the gel nail polish, and the first photoinitiator and second photoinitiator of the thinner, upon exposure to light activate to polymerize the gel nail polish.

5. The thinner of claim 4 wherein the first nonmetallic monomer comprises hydroxyethyl methacrylate and the second nonmetallic monomer comprises isobornyl methacrylate, and the percentage by weight of the hydroxyethyl methacrylate in the thinner is greater than the weight of isobornyl methacrylate.

6. The thinner of claim 4 wherein the first photoinitiator comprises hydroxycyclohexyl phenyl ketone and the second photoinitiator comprises 2, 4, 6-trimethylbenzoyldiphenylphosphine oxide, and the percentage by weight of the hydroxycyclohexyl phenyl ketone in the thinner is greater than the weight of 2, 4, 6-trimethylbenzoyldiphenylphosphine, and
the first photoinitiator is responsive to a light of a first ultraviolet wavelength, the second photoinitiator is responsive to a light of a second ultraviolet wavelength, which is different from the first ultraviolet wavelength, and
the polymerization reaction will occur when the thinner is subjected to ultraviolet light of at least one of the first or second ultraviolet wavelength.

7. The thinner of claim 4 wherein the first nonmetallic monomer comprises hydroxyethyl methacrylate and the second nonmetallic monomer comprises isobornyl methacrylate, the first photoinitiator comprises hydroxycyclohexyl phenyl ketone and the second photoinitiator comprises 2, 4, 6-trimethylbenzoyldiphenylphosphine oxide, the percentage by weight of the hydroxyethyl methacrylate in the thinner is greater than the weight of the isobornyl methacrylate, the hydroxycyclohexyl phenyl ketone, and the 2, 4, 6-trimethylbenzoyldiphenylphosphine oxide, and the percentage by weight of the hydroxycyclohexyl phenyl ketone in the thinner is greater than the weight of 2, 4, 6-trimethylbenzoyldiphenylphosphine.

8. The thinner of claim 4 comprising: a third monomer comprising alkoxylated diacrylate.

9. The thinner of claim 8 wherein before polymerization, the third monomer acts as a redispersant for a pigment in the gel nail polish, and during polymerization, the third monomer forms covalent bonds with chains of the first and second monomers to crosslink them together.

10. The thinner of claim 4 wherein the composition does not include any pigments.

11. A gel nail polish thinner comprising:
a first monomer comprising hydroxyethyl methacrylate, wherein the concentration of the first monomer is greater than the concentration of any other monomer in the composition;
a second monomer comprising alkoxylated diacrylate, wherein the ratio of the concentration of the first monomer to the concentration of the second monomer is in a range from about 25:1 to about 7:1; and
a first photoinitiator, wherein the composition is solvent free and does not include any oligomers, and the viscosity of the thinner is in the range of 0.01 poise to 2 poise,
before polymerization, the second monomer acts as a pigment redispersant for a pigment in a gel nail polish to which the thinner is added, and
during polymerization, the second monomer acts as a crosslinker to crosslink the polymer chains comprising the first monomer into a net-like polymeric structure.

12. The thinner of claim 11 wherein the composition does not include any pigments.

13. The thinner of claim 11 comprising:
the first monomer in the range of 25-35 percent by weight;
a third monomer comprising isobornyl methacrylate in the range of 20-30 percent by weight;
the first photoinitiator comprising hydroxycyclohexyl phenyl ketone in the range of 20-30 percent by weight, wherein hydroxycyclohexyl phenyl ketone is responsive to a light of a first ultraviolet wavelength; and
a second photoinitiator comprising 2, 4, 6-trimethylbenzoyldiphenylphosphine oxide in the range of 10-15 percent by weight, wherein 2, 4, 6-trimethylbenzoyldiphenylphosphine oxide is responsive to a light of a second ultraviolet wavelength, which is different from the first ultraviolet wavelength.

14. The thinner of claim 11 comprising a third monomer comprising ethoxylated trimethylolpropane triacrylate esters (ETPTA).

15. A gel nail polish thinner comprising:
a first monomer comprising hydroxyethyl methacrylate, wherein the concentration of the first monomer is greater than the concentration of any other ingredient in the composition;
a second monomer comprising alkoxylated diacrylate; and
a first photoinitiator,
wherein the composition does not comprise a solvent and does not include any oligomers, and the viscosity of the thinner is in the range of 0.01 poise to 2 poise,
before polymerization, the second monomer acts as a pigment redispersant for a pigment in a gel nail polish to which the thinner is added, and
during polymerization, the second monomer acts as a crosslinker to crosslink the polymer chains comprising the first monomer into a net-like polymeric structure.

16. The thinner of claim 15 wherein the first photoinitiator is responsive to a light of a first ultraviolet wavelength from about 370 nanometers to about 380 nanometers.

17. The thinner of claim 15 comprising a second photoinitiator, wherein the first photoinitiator comprises hydroxycyclohexyl phenyl ketone that is responsive to a light of a first ultraviolet wavelength,
the second photoinitiator comprises 2, 4, 6-trimethylbenzoyldiphenylphosphine oxide that is responsive to a light of a second ultraviolet wavelength, which is different from the first ultraviolet wavelength, and
a polymerization reaction will occur when the thinner is subjected to ultraviolet light of at least one of the first or second ultraviolet wavelength.

18. The thinner of claim 15 wherein the composition does not include any pigments.

19. A kit comprising:
a nonsolvent-based thinner for a gel nail polish comprising (i) only nonmetallic monomers comprising a first nonmetallic monomer, (ii) a first photoinitiator, and (iii) no oligomers, wherein the first photoinitiator is responsive to a light of a first ultraviolet wavelength, the viscosity of the thinner is in the range of about 1 centipoise to about 10 centipoise, wherein the thinner is added to the gel nail polish to reduce the viscosity of the gel nail polish;
a glass bottle to contain the thinner, wherein the glass bottle comprises a first glass color that blocks the transmission of light of the first ultraviolet wavelength, a bottle cap comprising an eyedropper, and a label; and
a box comprising a cut out to allow the label on the glass bottle to be visible while in the box.

20. The kit of claim 19 wherein the thinner comprises a second photoinitiator that is responsive to a light of a second ultraviolet wavelength, which is different from the first ultraviolet wavelength, and the first glass color blocks the transmission of light of the second ultraviolet wavelength.

21. The kit of claim 19 comprising:
a second nonmetallic monomer comprising alkoxylated diacrylate.

* * * * *